US00PP11192P

United States Patent [19]

Stemkens

[11] Patent Number: Plant 11,192

[45] Date of Patent: Jan. 25, 2000

[54] VERBENA PLANT NAMED 'MYLENA'

[75] Inventor: Henricus G. W. Stemkens, Hoorn, Netherlands

[73] Assignee: Novartis AG, Basel, Switzerland

[21] Appl. No.: 08/826,210

[22] Filed: Mar. 27, 1997

[51] Int. Cl.[7] ..... A01H 5/00

[52] U.S. Cl. ..... Plt./308

[58] Field of Search ..... Plt./87, 308

[56] References Cited

U.S. PATENT DOCUMENTS

P.P. 8,995 11/1994 Tachibana et al. ..... Plt./87

P.P. 9,085 3/1995 Tachibana et al. ..... Plt./87

P.P. 9,411 12/1995 Tachibana et al. ..... Plt./87

*Primary Examiner*—Howard J. Locker

*Assistant Examiner*—Kent L. Bell

*Attorney, Agent, or Firm*—Thomas Hoxie; J. Timothy Meigs

[57] ABSTRACT

A new and distinct variety of Verbena plant, named Mylena, characterized particularly as to novelty by large, early appearing, dark purple flowers, and a growth habit that is initially semi-erect but later spreading and hanging.

2 Drawing Sheets

BACKGROUND OF THE NEW PLANT

The present invention comprises a new distinct cultivar of Verbena, botanically known as *Verbena hybrida*. The new culltivar is propagated from cuttings resulting from the cross of 'R670' and 'R678'. 'R670' is a purple flowering Verbena having a spreading habit. 'R670' is not commercially available and is not known by any synonyms. 'R678' is a pink flowering Verbena having a semi-erect habit. 'R678' is not commercially available and is not known by any synonyms. Neither 'R670' or 'R678' has been patented. As a result of this cross the present cultivar was created in 1992 in Enkhuizen, Netherlands and has been repeatedly asexually reproduced by cuttings in Enkhuizen, Netherlands and Sarrians, France over three year period. It has been found to retain its distinctive characteristics through successive propagations, and this novelty appears to be firmly fixed.

DESCRIPTION OF THE DRAWINGS

This new Verbena plant is illustrated by the accompanying photographic drawings which show blooms and buds of the plant in full color, the color shown being as true as can be reasonably obtained by conventional photographic procedures. Flower and bud color may appear different from actual color due to light refraction.

The illustration on the first page shows a close up of a large, purple inflorescence of the plant in full bloom.

The illustration on the second page shows the mature plant exhibiting its characteristics spreading and hanging growth habit.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 week old plants, blossomed under natural light in a greenhouse. Color readings were taken in the greenhouse under ambient light. Color references are to the R.H.S. Colour Chart of The Royal Horticultural Society of London.

Plant:

*Classification.*—Botanical: *Verbena hybrida.*

*Parentage.*—Female parent: A seedling named 'R670'. Pollen parent: A seedling named 'R678'.

*Growth habit.*—Semi-erect, later spreading.

*Plant height.*—20–30 cm.

*Spreading area of plant.*—60–90 cm.

*Growth rate.*—Hanging and vigorous.

*Strength.*—Very good.

*Branching character.*—After pinching 6–8 breaks occur.

*Blooming period.*—From April until November.

Stem:

*Diameter.*—1.5–2.5 mm.

*Cross section.*—Tetragonal.

*Anthocyan pigmentation.*—Absent.

*Length of internode.*—25–60 mm, depending on the light where the plant is grown.

*Pubescence.*—Some pubescence is present.

Foliage:

*Phyllotaxis.*—Opposite.

*Shape of blade.*—Cleft to parted.

*Texture.*—Mostly smooth, slightly pubescent.

*Length.*—25–40 mm.

*Width.*—22–42 mm.

*Depth of incision.*—10–20 mm.

*Color.*—Upper side: Medium green 141A. Lower side: Light green 143A.

*Pubescence.*—Some pubescence is present on both sides of the leaf.

*Length of leaf stem.*—15–20 mm.

Bud:

*Peduncle length.*—40–70 mm, depending on season.

*Size.*—Diameter: 2 mm. Length: 8–12 mm.

*Shape.*—Elongated.

*Color.*—Medium green 141A.

*Sepals.*—Color: Green 137D. Form: Upright.

Flower:

*Direction.*—Ascending.

*Diameter.*—16–22 mm.

*Height.*—16–18 mm.

*Borne.*—In a cluster.
*Form.*—Flat and symmetrical.
*Cluster.*—Corymb.
*Color.*—Upper surface: Dark Purple 78B, later 78C, Lower surface: Purple 78C, later 78D.
*Eye.*—A very small (2 mm) green-white (157D) eye is present. Typically three out of the five petals exhibit this green-white coloration at their bases.
*Number of petals.*—5.
*Shape of the petals.*—Gametopetalous, grown together at the base of the petal. Each petal is heart-shaped at the top.
*Size of the petals.*—Length: 6–8 mm. Width: 5–7 mm.
*Overlapping of petals.*—Separate.
*Corymb.*—Length: 20–40 mm. Diameter: 40–50 mm.
*Calyx.*—Length of 10–12 mm.
*Anthocyan pigmentation of calyx limb.*—Absent.
*No. of flowers per corymb.*—20–40.
*Fragrance.*—A very soft rosy-sweet fragrance.
*Flowers in bloom at one time.*—Maximum 14.
*Longevity.*—Flower: 4–6 days. Inflorescence: 14–21 days.
*Reproductive organs.*—1 pistil, 5 stamens. Seeds are formed in a very low frequency.

Roots:

*Type of roots.*—Fibrous and adventitous. Roots grow on every part of the stem which contacts the soil, not only at the nodes.

Physiological and Ecological Characteristics

Good tolerance to heat and cold. Strong resistance to pests and diseases, particularly powdery mildew.

The new Verbena plant described herein is distinct from known Verbena plants in the characteristics described above, and is particularly distinguished by its large, early-appearing, dark purple flower and a growth habit which is initially semi-erect habit but becomes spreading and hanging as the plants develop. 'Mylena' is an annual in most climatic zones in the U.S., but may be perennial to zones 9 and 10. 'Mylena' is related to 'Silvena' and 'Morena', claimed in co-pending plant applications Ser. Nos. 08/826,211 and 08/828,020 respectively. 'Morena' was derived from the cross of 'R678' and 'R673', while 'Silvena' and 'Mylena' are full siblings derived from 'R670' and 'R678'. The flower color of 'Morena' is more pink (73B) than 'Mylena' (78B), while 'Silvena' is lighter and more blue (82A) in color. The plant habit differs somewhat between 'Mylena' and 'Silvena'. 'Mylena' is earlier to be semi-trailing, while 'Silvena' is later and stays upright longer.

What is claimed is:

1. A new and distinct variety of Verbena plant, substantially as herein illustrated and described, characterized particularly as to novelty by large, early appearing, dark purple flowers, and a growth habit that is initially semi-erect but later spreading and hanging.

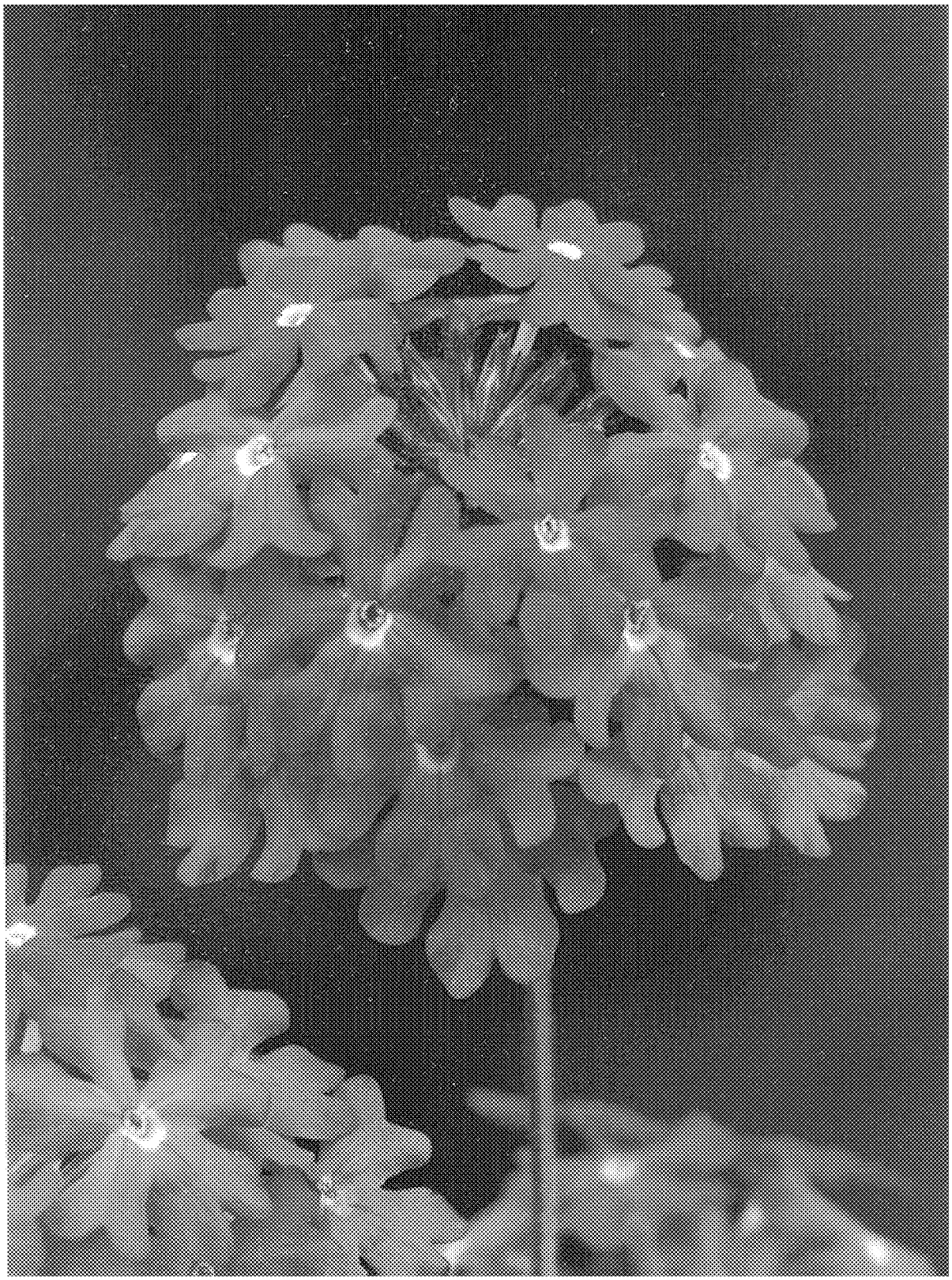

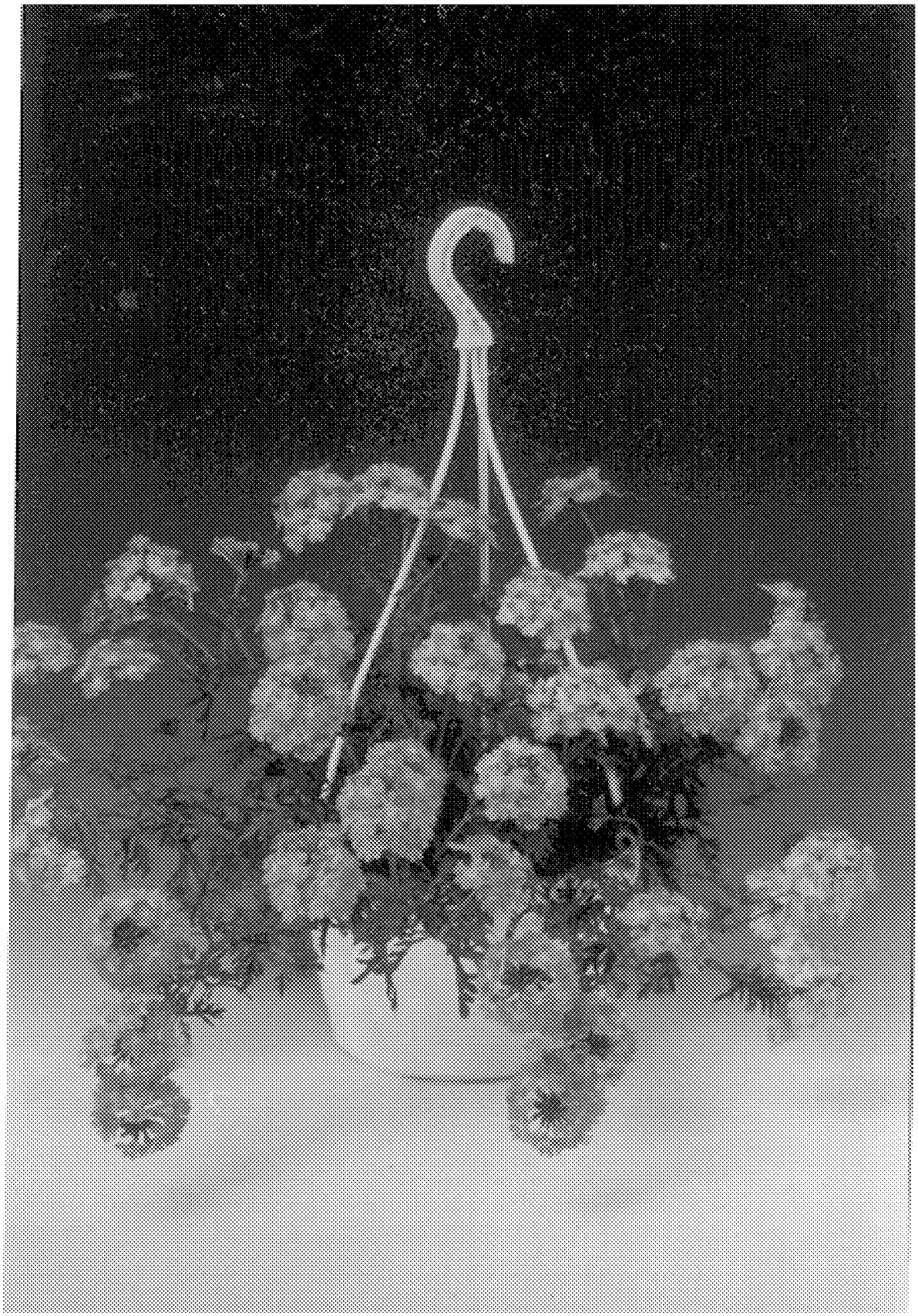

* * * * *